United States Patent
Koenemann et al.

(10) Patent No.: US 7,358,362 B2
(45) Date of Patent: Apr. 15, 2008

(54) METHOD FOR THE PRODUCTION OF TERYLENE-3,4:11,12-TETRACARBOXYDIIMIDES BY DIRECT SYNTHESIS

(75) Inventors: Martin Koenemann, Mannheim (DE); Arno Boehm, Mannheim (DE); Willi Helfer, Friedelsheim (DE); Juergen Romeis, Ludwigshafen (DE); Jianqiang Qu, Mannheim (DE); Klaus Muellen, Cologne (DE)

(73) Assignees: BASF Aktiengesellschaft, Ludwigshafen (DE); Maz-Planck-Gesellschaft zur Foerderung der Wissenschaften e.V., Munich (DE)

( * ) Notice: Subject to any disclaimer, the term of this patent is extended or adjusted under 35 U.S.C. 154(b) by 65 days.

(21) Appl. No.: 10/586,133

(22) PCT Filed: Jan. 15, 2005

(86) PCT No.: PCT/EP2005/000378

§ 371 (c)(1),
(2), (4) Date: Jul. 17, 2006

(87) PCT Pub. No.: WO2005/070895

PCT Pub. Date: Aug. 4, 2005

(65) Prior Publication Data

US 2007/0155968 A1   Jul. 5, 2007

(30) Foreign Application Priority Data

Jan. 23, 2004   (DE) ...................... 10 2004 003 734

(51) Int. Cl.
C07D 471/06 (2006.01)
C07D 221/18 (2006.01)

(52) U.S. Cl. .............................. 546/26; 546/41; 546/98

(58) Field of Classification Search .................. 546/26, 546/41, 98
See application file for complete search history.

(56) References Cited

FOREIGN PATENT DOCUMENTS

DE    195 12 773    10/1996

OTHER PUBLICATIONS

Holtrup et al., "Terrylenimides: New NIR Fluorescent Dyes", Chemistry—A European Journal, vol. 3, No. 2, pp. 219-225, 1997.
Weil et al., "Synthesis and Characterization of Dendritic Multichromophores Based on Rylene Dyes for Vectorial Transduction of Excitation Energy", Chemistry—A European Journal, vol. 10, No. 6, pp. 1398-1414, 2004.
Langhals et al., "A Two-Step Synthesis of Quaterrylenetetracarboxylic Bisimides-Novel NIR Fluorescent Dyes", Tetrahedron Letters, vol. 36, No. 36, pp. 6423-6424, 1995.

Primary Examiner—Charanjit S. Aulakh
(74) Attorney, Agent, or Firm—Oblon, Spivak, McClelland, Maier & Neustadt, P.C.

(57) ABSTRACT

A process for preparing terylene-3,4:11,12-tetracarboximides I

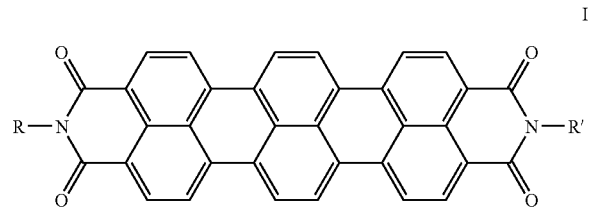

where the variables are each defined as follows:
R, R' are each independently hydrogen; if desired substituted alkyl or cycloalkyl;
$R^1$ is hydrogen or alkyl;
$R^2$ is hydrogen; alkyl; if desired substituted aryl or hetaryl, by reacting a perylene-3,4-dicarboximide II

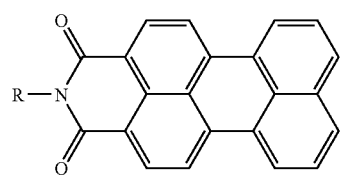

in the presence of a base-stable, high-boiling organic solvent and of an alkali metal or alkaline earth metal base, with a naphthalene-1,8-dicarboximide III

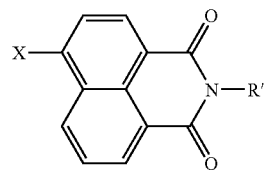

in which X is hydrogen, bromine or chlorine.

10 Claims, No Drawings

METHOD FOR THE PRODUCTION OF TERYLENE-3,4:11,12-TETRACARBOXYDIIMIDES BY DIRECT SYNTHESIS

The present invention relates to a novel process for preparing terylene-3,4:11,12-tetracarboximides of the general formula I

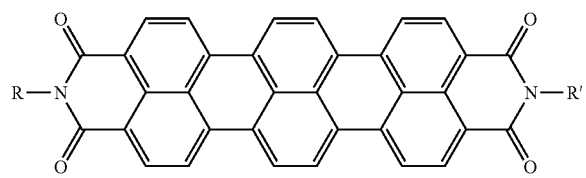

in which the variables are each defined as follows:

R, R' are each independently hydrogen;
- $C_1$-$C_{30}$-alkyl whose carbon chain may be interrupted by one or more —O—, —S—, —$NR^1$—, —CO— and/or —$SO_2$— moieties and which may be mono- or polysubstituted by cyano, $C_1$-$C_6$-alkoxy, aryl which may be substituted by $C_1$-$C_{18}$-alkyl or $C_1$-$C_6$-alkoxy, and/or a 5- to 7-membered heterocyclic radical bonded via a nitrogen atom which may contain further heteroatoms and be aromatic;
- $C_5$-$C_8$-cycloalkyl whose carbon skeleton may be interrupted by one or more —O—, —S— and/or —$NR^1$— moieties, and/or which may be mono- or polysubstituted by $C_1$-$C_6$-alkyl;
- aryl or hetaryl which may be mono- or polysubstituted by $C_1$-$C_{18}$-alkyl, $C_1$-$C_6$-alkoxy, cyano, halogen, —$CONHR^2$ and/or aryl- or hetarylazo, each of which may be substituted by $C_1$-$C_{10}$-alkyl, $C_1$-$C_6$-alkoxy or cyano;

$R^1$ is hydrogen or $C_1$-$C_6$-alkyl;

$R^2$ is hydrogen, $C_1$-$C_{18}$-alkyl; aryl or hetaryl, each of which may be substituted by $C_1$-$C_6$-alkyl, $C_1$-$C_6$-alkoxy, halogen, hydroxyl, carboxyl or cyano.

As is well known, terylene-3,4:11,12-tetracarboximides are suitable as pigments and fluorescence dyes with absorption in the long-wavelength red and fluorescence emission in the long-wavelength red to near infrared region of the electromagnetic spectrum.

Chem. Eur. J. 3, p. 219-225 (1997) describes a process for their preparation which starts from 5-bromoacenaphthoquinone and comprises a multitude of reaction steps, ketalization, conversion to a boronic acid, reaction with a 9-bromoperylene-3,4-dicarboximide in a Suzuki coupling reaction to give a 9-(4-acenaphthoquinonyl)-perylene-3,4-dicarboximide, oxidation to the tetracarboximide anhydride, imidation to the diimide and cyclodehydrogenation to the terylene-3,4:11,12-tetracarboximide.

According to Heterocycles 56, p. 331-340 (2002), N,N'-dialkyl-substituted terylene-3,4:11,12-tetracarboximides are obtainable by converting an N-alkyl-9-bromoperylene-3,4-dicarboximide to the 9-tributyltin derivative, which is then coupled with an N-alkyl-4-halonaphthalene-1,8-dicarboximide to give the corresponding 9-(4-naphthalene-1,8-dicarboximide)perylene-3,4-dicarboximide, from which the terylene-3,4:11,12-tetracarboximide is in turn prepared by cyclodehydrogenation.

The known preparation processes have a series of disadvantages: toxic tin compounds and/or strong bases are used in large amounts, the reaction times are very long, and/or the overall yield is below 50%.

It is therefore an object of the invention to remedy these disadvantages and to provide a process which enables the preparation of terylene-3,4:11,12-tetracarboximides in an advantageous, economically viable manner.

Accordingly, a process has been found for preparing terylene-3,4:11,12-tetracarboximides of the general formula I

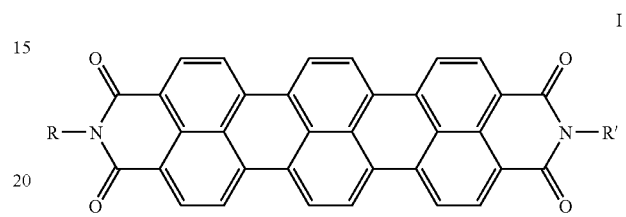

in which the variables are each as defined at the outset, which comprises reacting a perylene-3,4-dicarboximide of the general formula II

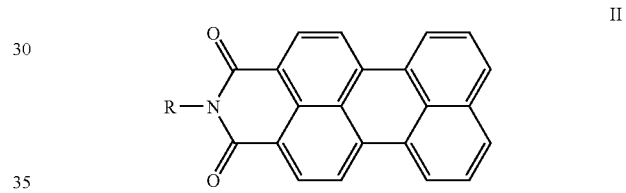

in the presence of a base-stable, high-boiling organic solvent and of an alkali metal or alkaline earth metal base, with a naphthalene-1,8-dicarboximide of the general formula III

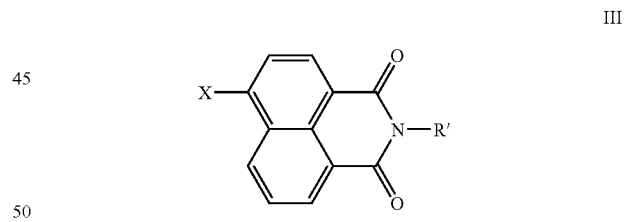

in which X is hydrogen, bromine or chlorine.

All alkyl groups occurring in the formulae I to III may be straight-chain or branched. When the alkyl groups are substituted, they generally bear 1 or 2 substituents.

Cycloalkyl groups and aromatic radicals which are substituted may generally have up to 3, preferably 1 or 2, of the substituents mentioned.

Specific examples of suitable R, R', $R^1$, $R^2$ and $R^3$ radicals (or their substituents) are as follows:

methyl, ethyl, propyl, isopropyl, butyl, isobutyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above terms isooctyl, isononyl, isodecyl and isotridecyl are trivial terms and stem from the alcohols obtained by the oxo process);

methoxymethyl, 2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxatridecyl and 3,6,9,12-tetraoxatetradecyl;

methylthiomethyl, 2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiatridecyl and 3,6,9,12-tetrathiatetradecyl;

2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazatridecyl and 3,6,9,12-tetramethyl-3,6,9,12-tetraazatridecyl;

propan-2-on-1-yl, butan-3-on-1-yl, butan-3-on-2-yl and 2-ethylpentan-3-on-1-yl;

2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl;

cyanomethyl, 2-cyanoethyl, 3-cyanopropyl, 2-methyl-3-ethyl-3-cyanopropyl, 7-cyano-7-ethylheptyl and 4,7-dimethyl-7-cyanoheptyl;

methoxy, ethoxy, propoxy, isopropoxy, butoxy, isobutoxy, sec-butoxy, tert-butoxy, pentoxy, isopentoxy, neopentoxy, tert-pentoxy and hexoxy;

carbamoyl, methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, decylaminocarbonyl and phenylaminocarbonyl;

chlorine, bromine and iodine;

phenylazo, 2-napthylazo, 2-pyridylazo and 2-pyrimidylazo;

phenyl, 1- and 2-naphthyl, 2- and 3-pyrryl, 2-, 3- and 4-pyridyl, 2-, 4- and 5-pyrimidyl, 3-, 4- and 5-pyrazolyl, 2-, 4- and 5-imidazolyl, 2-, 4- and 5-thiazolyl, 3-(1,2,4-triazyl), 2-(1,3,5-triazyl), 6-quinaldyl, 3-, 5-, 6- and 8-quinolinyl, 2-benzoxazolyl, 2-benzothiazolyl, 5-benzothiadiazolyl, 2- and 5-benzimidazolyl and 1- and 5- isoquinolyl;

2-, 3- and 4-methylphenyl, 2,3-, 2,4-, 2,5-, 3,5- and 2,6-dimethylphenyl, 2,4,6-trimethylphenyl, 2-, 3- and 4-ethylphenyl, 2,3-, 2,4-, 2,5-, 3,5- and 2,6-diethylphenyl, 2,4,6-triethylphenyl, 2-, 3- and 4-propylphenyl, 2,3-, 2,4-, 2,5-, 3,5- and 2,6-dipropylphenyl, 2,4,6-tripropylphenyl, 2-, 3- and 4-isopropylphenyl, 2,3-, 2,4-, 2,5-, 3,5- and 2,6-diisopropylphenyl, 2,4,6-triisopropylphenyl, 2-, 3- and 4-butylphenyl, 2,3-, 2,4-, 2,5-, 3,5- and 2,6-dibutylphenyl, 2,4,6-tributylphenyl, 2-, 3-and 4-isobutylphenyl, 2,3-, 2,4-, 2,5-, 3,5- and 2,6-diisobutylphenyl, 2,4,6-triisobutylphenyl, 2-, 3- and 4-sec-butylphenyl, 2,3-, 2,4-, 2,5-, 3,5- and 2,6-di-sec-butylphenyl and 2,4,6-tri-sec-butylphenyl, 2-, 3- and 4-tert-butylphenyl, 2,3-, 2,4-, 2,5-, 3,5- and 2,6-di-tert-butylphenyl, 2,4,6-tri-tert-butylphenyl; 2-, 3- and 4-methoxyphenyl, 2,3-, 2,4-, 2,5-, 3,5- and 2,6-dimethoxyphenyl, 2,4,6-trimethoxyphenyl, 2-, 3- and 4-ethoxyphenyl, 2,3-, 2,4-, 2,5-, 3,5- and 2,6-diethoxyphenyl, 2,4,6-triethoxyphenyl, 2-, 3- and 4-propoxyphenyl, 2,3-, 2,4-, 2,5-, 3,5- and 2,6-dipropoxyphenyl, 2-, 3- and 4-isopropoxyphenyl, 2,3-, 2,4-, 2,5-, 3,5- and 2,6-diisopropoxyphenyl and 2-, 3- and 4-butoxyphenyl; 2-, 3- and 4-chlorophenyl, and 2,3-, 2,4-, 2,5-, 3,5- and 2,6-dichlorophenyl; 2-, 3- and 4-hydroxyphenyl and 2,3-, 2,4-, 2,5-, 3,5- and 2,6-dihydroxyphenyl; 2-, 3- and 4-cyanophenyl; 3- and 4-carboxyphenyl; 3- and 4-carboxamidophenyl, 3- and 4-N-methylcarboxamidophenyl and 3- and 4-N-ethylcarboxamidophenyl; 3- and 4-acetylaminophenyl, 3- and 4-propionylaminophenyl and 3- and 4-butyrylaminophenyl; 3- and 4-N-phenylaminophenyl, 3- and 4-N-(o-tolyl)-aminophenyl, 3- and 4-N-(m-tolyl)aminophenyl and 3- and 4-N-(p-tolyl)aminophenyl; 3- and 4-(2-pyridyl)aminophenyl, 3- and 4-(3-pyridyl)aminophenyl, 3- and 4-(4-pyridyl)aminophenyl, 3- and 4-(2-pyrimidyl)aminophenyl and 4-(4-pyrimidyl)aminophenyl;

4-phenylazophenyl, 4-(1-naphthylazo)phenyl, 4-(2-naphthylazo)phenyl, 4-(4-naphthylazo)phenyl, 4-(2-pyridylazo)phenyl, 4-(3-pyridylazo)phenyl, 4-(4-pyridylazo)phenyl, 4-(2-pyrimidylazo)phenyl, 4-(4-pyrimidylazo)phenyl and 4-(5-pyrimidylazo)phenyl;

cyclopentyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methylcycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl, 3-, 4- and 5-propylcyclooctyl, 2-dioxanyl, 4-morpholinyl, 2- and 3-tetrahydrofuryl, 1-, 2- and 3-pyrrolidinyl and 1-, 2-, 3- and 4-piperidyl.

With the aid of the process according to the invention, it is possible to prepare the terylene-3,4:11,12-tetracarboximides I by reacting a perylene-3,4-dicarboximide II with a naphthalene-1,8-dicarboximide III in one step.

The inventive reaction is carried out in the presence of a base-stable, high-boiling organic solvent and of an alkali metal base.

The reactant used may be either 4-halogenated, i.e. -chlorinated or -brominated, or nonhalogenated naphthalene-1,8-dicarboximide III.

When nonhalogenated naphthalene-1,8-dicarboximide III is used, it is generally recommended to undertake the reaction under more severe reaction conditions, i.e. to use greater excesses of naphthalene-1,8-dicarboximide III and, in addition to a strong alkali metal base, a nitrogen auxiliary base and polar-aprotic solvent.

Accordingly, the molar ratio of naphthalene-1,8-dicarboximide III to perylene-3,4-dicarboximide II when halogenated reactant III is used (X: chlorine or bromine) is typically from 4 to 1:1 and preferably from 2 to 1:1, whereas, in the case of nonhalogenated reactant III, it is generally from 8 to 1:1 and preferably from 6 to 2:1.

Suitable solvents are in principle all high-boiling solvents stable against bases under the reaction conditions (boiling point >100° C. and above the reaction temperature selected), in which the perylene-3,4-dicarboximides II and the naphthalene-1,8-dicarboximides III dissolve fully at reaction temperature and the bases used at least partly, so that there are substantially homogeneous reaction conditions. Particularly suitable solvents are nonpolar-aprotic and polar-aprotic solvents, although preference is given to the nonpolar-aprotic solvents and aprotic solvents based on ethers when halogenated reactants III are used, and to the polar-aprotic solvents when nonhalogenated reactants III are used. However, it is also possible to use protic solvents, preferably those which have amino and hydroxyl functions. It will be appreciated that solvent mixtures may also be used.

Examples of particularly suitable nonpolar-aprotic solvents are solvents boiling at >100° C. from the following groups: aliphatics (in particular $C_8$-$C_{18}$-alkanes), unsubstituted, alkyl-substituted and fused cycloaliphatics (especially unsubstituted $C_7$-$C_{10}$-cycloalkanes, $C_6$-$C_8$-cycloalkanes which are substituted by from one to three $C_1$-$C_6$-alkyl groups, polycyclic saturated hydrocarbons having from 10 to 18 carbon atoms), alkyl- and cycloalkyl-substituted aromatics (especially benzene which is substituted by from one to three $C_1$-$C_6$-alkyl groups or a $C_5$-$C_8$-cycloalkyl radical) and fused aromatics which may be alkyl-substituted and/or partly hydrogenated (especially naphthalene which is substituted by from one to four $C_1$-$C_6$-alkyl groups), and also mixtures of these solvents.

Specific examples of preferred nonpolar-aprotic solvents include: octane, isooctane, nonane, isononane, decane, isodecane, undecane, dodecane, hexadecane and octadecane; cycloheptane, cyclooctane, methylcyclohexane, dimethylcyclohexane, trimethylcyclohexane, ethylcyclohexane, diethylcyclohexane, propylcyclohexane, isopropylcyclohexane, dipropylcyclohexane, butylcyclohexane, tert-butylcyclohexane, methylcycloheptane and methylcyclooctane; toluene, o-, m- and p-xylene, 1,3,5-trimethylbenzene(mesitylene), 1,2,4- and 1,2,3-trimethylbenzene, ethylbenzene, propylbenzene, isopropylbenzene, butylbenzene, isobutylbenzene, tert-butylbenzene and cyclohexylbenzene; naphthalene, decahydronaphthalene(decalin), 1- and 2-methylnaphthalene, 1- and 2-ethylnaphthalene; combinations of the aforementioned solvents, as may be obtained from the high-boiling, partly or fully hydrogenated fractions of thermal and catalytic cracking processes in crude oil or naphtha processing, for example mixtures of the Exxsol® type, and alkylbenzene mixtures of the Solvesso® type.

Particularly preferred nonpolar-aprotic solvents are xylene (all isomers), mesitylene and in particular toluene and decalin.

Examples of particularly suitable polar-aprotic solvents are N,N-disubstituted aliphatic carboxamides (especially N,N-di-$C_1$-$C_4$-alkyl-$C_1$-$C_4$-carboxamides), nitrogen-containing heterocycles, trialkylamines (especially tri($C_3$-$C_6$-alkyl)amines) and aprotic ethers (especially cyclic ethers, diaryl ethers and di-$C_1$-$C_6$-alkyl ethers of monomeric and oligomeric $C_2$-$C_3$-alkylene glycols which may contain up to 6 alkylene oxide units, in particular diethylene glycol di-$C_1$-$C_4$-alkyl ethers).

Specific examples of preferred polar-aprotic solvents are: N,N-dimethylformamide, N,N-diethylformamide, N,N-dimethylacetamide and N,N-dimethylbutyramide; N-methyl-2-pyrrolidone, quinoline, isoquinoline, quinaldine, pyrimidine, N-methylpiperidine and pyridine; tripropyl- and tributylamine; di and tetramethyl tetrahydrofuran, dioxane, diphenyl ether, the dimethyl, diethyl, dipropyl, diisopropyl, di-n-butyl, di-sec-butyl and di-tert-butyl ethers of diethylene glycol, diethylene glycol methyl ethyl ether, triethylene glycol dimethyl and diethyl ether and triethylene glycol methyl ethyl ether, and particular preference is given to diethylene glycol diethyl ether, diphenyl ether and especially to diethylene glycol dimethyl ether.

Particularly suitable protic solvents contain amino and hydroxyl functions. Examples of preferred protic solvents are alcoholamines, in particular mono-, di- and tri-$C_2$-$C_4$-alcoholamines, such as mono-, di- and triethanolamine, of which particular preference is given to ethanolamine.

The amount of solvent is generally from 50 to 250 ml of nonpolar-aprotic solvent, from 10 to 50 ml of polar-aprotic solvent or from 3 to 50 ml of protic solvent, per g of perylene-3,4-dicarboximide II.

Suitable bases are strong inorganic and organic alkali metal or alkaline earth metal bases, of which the alkali metal bases are particularly suitable. Preferred inorganic bases are alkali metal and alkaline earth metal hydroxides and amides; preferred organic bases are alkali metal and alkaline earth metal alkoxides (especially the $C_1$-$C_{10}$-alkoxides, in particular tert-$C_4$-$C_6$-alkoxides), alkali metal and alkaline earth metal (phenyl)alkylamides (especially the bis($C_1$-$C_4$-alkyl) amides) and triphenylmethyl metalates. Particular preference is given to the alkali metal alkoxides. Preferred alkali metals are lithium, sodium and potassium, of which very particular preference is given to potassium. Particularly suitable alkaline earth metals are magnesium and calcium.

Specific examples of particularly preferred bases include: lithium hydroxide, sodium hydroxide and potassium hydroxide; lithium amide, sodium amide and potassium amide; lithium methoxide, sodium methoxide, potassium methoxide, lithium ethoxide, sodium ethoxide, potassium ethoxide, sodium isopropoxide, potassium isopropoxide, sodium tert-butoxide, potassium tert-butoxide, lithium 1,1-dimethyloctoxide, sodium 1,1-dimethyloctoxide and potassium 1,1-dimethyloctoxide; lithium dimethylamide, lithium diethylamide, lithium diisopropylamide, sodium diisopropylamide, triphenylmethyllithium, triphenylmethylsodium and triphenylmethylpotassium. It will be appreciated that it is also possible to use mixtures of different bases.

Very particularly preferred bases are lithium diisopropylamide, sodium methoxide, sodium tert-butoxide, in particular potassium methoxide and potassium hydroxide and especially potassium tert-butoxide.

When the methoxides and the hydroxides are used, and also generally when non-halogenated reactants III are used, it is recommended to increase the reactivity by adding a nitrogen auxiliary base having lesser nucleophilic action. Suitable bases are alkylamines liquid at the reaction temperatures, especially tri-$C_3$-$C_6$-alkylamines such as tripropylamine and tributylamine, alcoholamines, especially mono-, di- and tri-$C_2$-$C_4$-alcoholamines such as mono-, di- and triethanolamine, and especially heterocyclic bases such as pyridine, N-methylpiperidine, N-methylpiperidone, N-methylmorpholine, N-methyl-2-pyrrolidone, pyrimidine, quinoline, isoquinoline, quinaldine and in particular diazabicyclononene (DBN) and diazabicycloundecene (DBU). It will be appreciated that it is also possible to use mixtures of these auxiliary bases.

Suitable use amounts for the auxiliary base in the case of the halogenated reactants III are generally from 1 to 15 g, preferably from 1 to 5 g, per g of perylene-3,4-dicarboximide II and, in the case of the nonhalogenated reactants III, generally from 1 to 60 g, preferably from 5 to 30 g, per g of perylene-3,4-dicarboximide II. In the case of halogenated reactants III, typically from 2 to 10 mol, especially from 2 to 4 mol, of alkali metal base are used per mole of perylene-3,4-dicarboximide II and, in the case of nonhalogenated reactants III, generally from 2 to 20 mol, preferably from 8 to 20 mol, per mole of perylene-3,4-dicarboximide II.

The alkali metal base may be used in solid or in dissolved form. When the alkali metal base is used in combination with a nonpolar-aprotic reaction solvent in which it is not sufficiently soluble, it may be dissolved in an alcohol which has a higher base strength than the alkali metal base. Suitable are in particular tertiary aliphatic alcohols which may contain aryl substituents and have a total of from four to twelve carbon atoms, for example tert-butanol, 2-methyl-2-butanol (tert-amyl alcohol), 3-methyl-3-pentanol, 3-ethyl-3-pentanol, 2-phenyl-2-pentanol, 2,3-dimethyl-3-pentanol, 2,4,4-trimethyl-2-pentanol and 2,2,3,4,4-pentamethyl-3-pentanol.

The reaction temperature is typically from 50 to 210° C., preferably from 70 to 180° C. Especially in the absence of an auxiliary base, it may be advantageous to initially select a reaction temperature in the upper range in order to deprotonate the perylene-3,4-dicarboximide II in the 9-position. The subsequent coupling reaction with the naphthalene-1,8-dicarboximide III may then generally be carried out at lower temperature, which is recommended especially in the case of naphthalene-1,8-dicarboximides III having base-labile substituents (e.g. cyclohexyl) on the imide nitrogen atom.

The reaction time is generally from 1 to 3 hours in the case of halogenated reactants III and from 2 to 8 hours in the case of nonhalogenated reactants III.

In terms of process technology, the procedure when nonhalogenated reactants III are used is appropriately as follows:

Perylene-3,4-dicarboximide II, naphthalene-1,8-dicarboximide III and a base are initially charged, solvent and, if appropriate, auxiliary base are added under protective gas and the mixture is heated for the desired time with stirring and under protective gas to the desired reaction temperature. After cooling to room temperature, the terylene-3,4:11,12-tetracarboximides I are precipitated by adding a protic solvent which dissolves the other components, for example $C_1$-$C_3$-alcohols and especially water. The precipitate is filtered off and washed with one of the solvents mentioned, especially with one of the alcohols.

When halogenated reactants III are used, the procedure may be similar. However, it is also possible to heat initially only a mixture of perylene-3,4-dicarboximide II, base, if appropriate auxiliary base and solvent with stirring and under protective gas to a temperature in the range from 120 to 210° C. (deprotonation) and then add the naphthalene-1,8-dicarboximide III subsequently, if appropriate after reducing the temperature from 50 to 120° C.

It may occasionally be appropriate to subject the reaction product to an oxidation. This may be effected in the simplest way by blowing atmospheric oxygen into the still-warm reaction mixture. However, it is also possible to add oxidizing agents, preferably hydrogen peroxide, but also aldehydic sugars, for example glucose.

For further purification, the products I can, for example, be recrystallized from a mixture of halogenated solvents such as chloroform and methylene chloride, and alcohols such as methanol, ethanol and isopropanol, or from a carboxamide such as N-methylpyrrolidone. Alternatively, column chromatography may also be undertaken on silica gel using methylene chloride or acetone as the eluent.

With the aid of the process according to the invention, it is possible to prepare the terylene-3,4:11,12-tetracarboximides I in good yields (generally from 50 to 80% when halogenated reactants are used and from 25 to 70% when the nonhalogenated reactant III is used) and high purities (typically from 95 to 99%) in an economically viable manner in one step. Terylene-3,4:11,12-tetracarboximides I substituted either symmetrically or unsymmetrically on the amide nitrogen atoms are obtainable in an advantageous manner.

EXAMPLES

Examples 1 to 7

A mixture of 10 mmol of the perylene-3,4-dicarboximide II, x ml of the solvent S and, if appropriate, b g of diazabicycloundecene (DBU) as an auxiliary base were heated to $T_1°$ C. in a nitrogen atmosphere with stirring, admixed within 30 min with a total of m mmol of the base B (example 1 to 6: B dissolved in 100 ml of 2-methylbutanol; example 7: B as a solid). After a continued stirring time of $t_1$ h at $T_1°$ C. and cooling to $T_2°$ C., a total of 150 ml of a solution of 15 mmol (example 5: 18 mmol) of the 4-bromonaphthalimide III in the solvent S were added at this temperature in portions within 30 min.

After a continued stirring time of $t_2$ h at $T_2°$ C. under air, cooling to room temperature and, if appropriate, addition of 300 ml of methanol for complete precipitation, the precipitate formed was filtered off, washed successively with cold solvent S, petroleum ether and methanol until the effluent was colorless, and dried at 100° C. under reduced pressure. For further purification, the crude product from example 1 to 4 and also 6 and 7 was subjected to column chromatography on silica gel using methylene chloride as the eluent and the crude product from example 5 to a fractional crystallization from sulfuric acid.

Further details on these experiments and their results are compiled in a table which follows.

In the table:
IIa: N-(2,6-Diisopropylphenyl)perylene-3,4-dicarboximide
IIb: N-Methylperylene-3,4-dicarboximide
IIc: N-Cyclohexylperylene-3,4-dicarboximide
IIIa: 4-Bromo-N-(2,6-diisopropylphenyl)naphthalene-1,8-dicarboximide
IIIb: 4-Bromo-N-cyclohexylnapthalene-1,8-dicarboximide
IIIc: 4-Bromo-N-methylnaphthalene-1,8-dicarboximide
B1: Potassium tert-butoxide
B2: Potassium methoxide
B3: Potassium hydroxide
DGDME: Diethylene glycol dimethyl ether

Example 8

10 mmol of N-(2,6-diisopropylphenyl)perylene-3,4-dicarboximide, 40 mmol of N-(2,6-diisopropylphenyl)naphthalene-1,8-dicarboximide and 0.2 mol of sodium tert-butoxide were dissolved under nitrogen in 30 ml of diazabicyclononene (DBN) and 25 ml of diethyl glycol dimethyl ether and heated to 130° C.

After stirring at this temperature for three hours and cooling to room temperature, the reaction mixture was added to 100 ml of water. The precipitate was filtered off and washed with ethanol until the filtrate running off had a reddish color. After recrystallization in a chloroform/ethanol mixture, 3.5 g of blue product were obtained, which corresponds to a yield of 42%.

Example 9

The procedure was similar to example 8, except that 0.4 mol of sodium tert-butoxide and 60 ml of DBU, and also 50 ml of ethanolamine instead of diethyl glycol dimethyl ether, were used and the reaction time was 6 h.

2.3 g of product were obtained, which corresponds to a yield of 28%.

TABLE

| Ex. | Reactant II | x [ml] | Solv. S | DBU b [g] | $T_1$ [° C.] | m [mmol] | Base B | $t_1$ [h] | $T_2$ [° C.] | Reactant III | $t_2$ [h] | Yield [g]/[%] | Purity [%] | m.p. [° C.] | Appearance |
|---|---|---|---|---|---|---|---|---|---|---|---|---|---|---|---|
| 1 | IIa | 800 | Decalin | — | 160 | 40 | B1 | 0.5 | 100 | IIIa | 1 | 4.9/58 | >98 | >300 | black-blue, crystalline |
| 2 | IIa | 800 | Decalin | — | 160 | 40 | B1 | — | 90 | IIIb | 0.5 | 4.9/64 | >98 | >300 | dark blue, microcrystalline |
| 3 | IIa | 800 | Decalin | 15 | 165 | 25 | B1 | 0.25 | 100 | IIIc | 1 | 4.9/71 | >95 | >300 | black-blue, crystalline |
| 4 | IIb | 100 | Diphenyl ether | 10 | 180 | 30 | B2 | 0.5 | 80 | IIIb | 0.5 | 4.2/68 | >95 | >300 | dark blue, amorphous |
| 5 | IIb | 75 | DGDME | 10 | 180 | 30 | B1 | 0.25 | 100 | IIIc | 2 | 4.0/73 | >90 | >300 | black, crystalline |
| 6 | IIc | 700 | Decalin | — | 160 | 40 | B1 | 0.25 | 80 | IIIb | 0.5 | 3.7/55 | >98 | >300 | dark blue, amorphous |
| 7 | IIc | 50 | DGDME | 12 | 150 | 40 | B3 | 0.5 | 80 | IIIc | 1 | 3.8/62 | >95 | >300 | black-blue, crystalline |

What is claimed is:

1. A process for preparing terylene-3,4:11,12-tetracarboximides of the general formula I

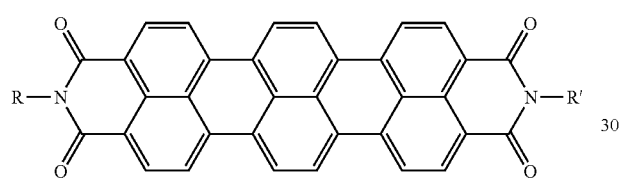

in which the variables are each defined as follows:

R, R' are each independently hydrogen;

$C_1$-$C_{30}$-alkyl whose carbon chain may be interrupted by one or more —O—, —S—, —NR$^1$—, —CO— and/or —SO$_2$— moieties and which may be mono- or polysubstituted by cyano, $C_1$-$C_6$-alkoxy, aryl which may be substituted by $C_1$-$C_{18}$-alkyl or $C_1$-$C_6$-alkoxy, and/or a 5- to 7-membered heterocyclic radical bonded via a nitrogen atom which may contain further heteroatoms and be aromatic;

$C_5$-$C_8$-cycloalkyl whose carbon skeleton may be interrupted by one or more —O—, —S— and/or —NR$^1$— moieties, and/or which may be mono- or polysubstituted by $C_1$-$C_6$-alkyl;

aryl or hetaryl which may be mono- or polysubstituted by $C_1$-$C_{18}$alkyl, $C_1$-$C_6$-alkoxy, cyano, halogen, —CONHR$^2$ and/or aryl- or hetarylazo, each of which may be substituted by $C_1$-$C_{10}$-alkyl, $C_1$-$C_6$-alkoxy or cyano;

$R^1$ is hydrogen or $C_1$-$C_6$-alkyl; and $R^2$ is hydrogen, $C_1$-$C_{18}$-alkyl; aryl or hetaryl, each of which may be substituted by $C_1$-$C_6$-alkyl, $C_1$-$C_6$-alkoxy, halogen, hydroxyl, carboxyl or cyano, which comprises reacting a perylene-3,4-dicarboximide of the general formula II

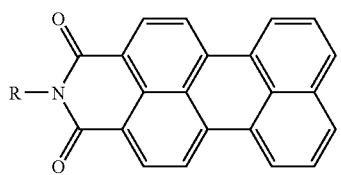

in the presence of a base-stable, high-boiling organic solvent and an alkali metal or alkaline earth metal base, with a naphthalene-1,8-dicarboximide of the general formula III

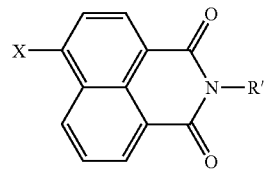

in which X is hydrogen, bromine or chlorine.

2. The process according to claim 1, wherein the organic solvent is an aprotic organic solvent.

3. The process according to claim 1, wherein the organic solvent is a polar-aprotic organic solvent.

4. The process according to claim 1, wherein the organic solvent is a nonpolar-aprotic organic solvent.

5. The process according to claim 1, wherein the organic solvent is a protic organic solvent.

6. The process according to claim 1, wherein the organic solvent is a solvent containing amino and hydroxyl functions.

7. The process according to claim 1, wherein the base used is a strong inorganic or organic alkali metal base.

8. The process according to claim 1, wherein the base used is an alkali metal alkoxide.

9. The process according to claim 1, wherein a nitrogen base having lesser nucleophilic action is additionally used as an auxiliary base.

10. The process according to claim 1, wherein the reaction is undertaken at temperatures ranging from 50 to 210° C.

* * * * *

UNITED STATES PATENT AND TRADEMARK OFFICE
CERTIFICATE OF CORRECTION

PATENT NO. : 7,358,362 B2  
APPLICATION NO. : 10/586133  
DATED : April 15, 2008  
INVENTOR(S) : Koenemann et al.

Page 1 of 1

It is certified that error appears in the above-identified patent and that said Letters Patent is hereby corrected as shown below:

On the title page, Item (73), the 2$^{ND}$ Assignee's information is incorrect. Item (73) should read:

-- (73)    Assignees:    BASF Aktiengesellschaft,  
Ludwigshafen (DE);  
Max-Planck-Gesellschaft zur Foerderung der Wissenschaften e.V.,  
Muenchen (DE) --

Signed and Sealed this

Eighth Day of July, 2008

JON W. DUDAS  
*Director of the United States Patent and Trademark Office*